United States Patent [19]

Inomata et al.

[11] Patent Number: 4,996,344

[45] Date of Patent: Feb. 26, 1991

[54] FLUORINE-CONTAINING ORGANOSILICON COMPOUND AND PROCESS FOR PREPARING THE SAME

[75] Inventors: Hiroshi Inomata, Takasaki; Hirofumi Kishita, Annaka; Akira Yoshida, Tokyo, all of Japan

[73] Assignee: Shin-Etsu Chemical Co., Ltd., Tokyo, Japan

[21] Appl. No.: 308,466

[22] Filed: Feb. 10, 1989

[30] Foreign Application Priority Data

Feb. 12, 1988 [JP] Japan .................................. 63-32474

[51] Int. Cl.$^5$ ................................................ C07F 7/08
[52] U.S. Cl. ................................................................. 556/448
[58] Field of Search ........................................ 556/448

[56] References Cited

U.S. PATENT DOCUMENTS

| | | | |
|---|---|---|---|
| 3,331,813 | 7/1967 | Pittman et al. | 556/448 X |
| 3,420,793 | 1/1969 | Pittman et al. | 556/448 X |
| 3,422,131 | 1/1969 | Pittman et al. | 556/448 |
| 3,423,234 | 1/1969 | Heine | 556/448 X |
| 3,529,003 | 9/1970 | Rauech et al. | 556/448 |
| 3,876,677 | 4/1975 | Wu | 556/448 |

*Primary Examiner*—Paul F. Shaver
*Attorney, Agent, or Firm*—Oblon, Spivak, McClelland, Maier & Neustadt

[57] ABSTRACT

A fluorine-containing organosilicon compound represented by Formula (I):

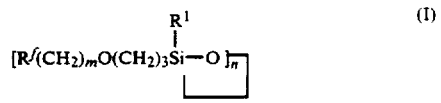

wherein $R^1$ represents a monovalent hydrocarbon group having 1 to 10 carbon atoms; $R^f$ represents a fluorine-containing group represented by the formula: $C_pF_{2p+1}-$, where p is an integer of 3 to 6,

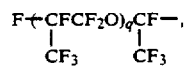

where q is an integer of 1 or 2, or

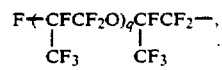

where q is as defined above; m is an integer of 0 to 2; and n is an integer of 3 or 4.

This novel compound is useful for the preparation of fluorosilicone polymers having a good thermal resistance, chemical resistance and weathering resistance.

4 Claims, 5 Drawing Sheets

FLUORINE-CONTAINING ORGANOSILICON COMPOUND AND PROCESS FOR PREPARING THE SAME

BACKGROUND OF THE INVENTION

1. Field of the Invention

This invention relates to a novel fluorine-containing organosilicon compound, and particularly it is concerned with a fluorine-containing organosilicon compound. Which is useful as a starting material for fluorosilicone fluids or elastomers having a good thermal resistance, chemical resistance, weathering resistance, etc.

2. Description of the Prior Art

Compounds like the fluorine-containing organosilicon compound provided by this invention are not believed to have been hitherto described.

SUMMARY OF THE INVENTION

An object of this invention is to originally provide a novel fluorine-containing organosilicon compound, which compound is useful as a starting material for fluorosilicone fluids or elastomers having a high thermal resistance, chemical resistance and weathering resistance, and having a small surface energy and a low refractive index.

The novel fluorine-containing organosilicon compound provided by this invention is a compound represented by Formula (I):

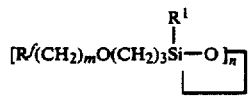

wherein $R^1$ represents a monovalent hydrocarbon group having 1 to 10 carbon atoms; $R^f$ represents a fluorine-containing group represented by the formula: $C_pF_{2p+1}-$, where p is an integer of 3 to 6,

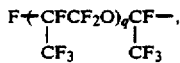

where q is an integer of 1 or 2, or

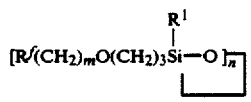

where q is as defined above; m is an integer of 0 to 2 and n is an integer of 3 or 4.

The fluorine-containing organosilicon compound according to this invention is a novel substance, which is useful for the preparation of fluorosilicone polymers having a good thermal resistance, chemical resistance and weathering resistance.

DETAILED DESCRIPTION OF PREFERRED EMBODIMENTS OF THE INVENTION

Figure 1:
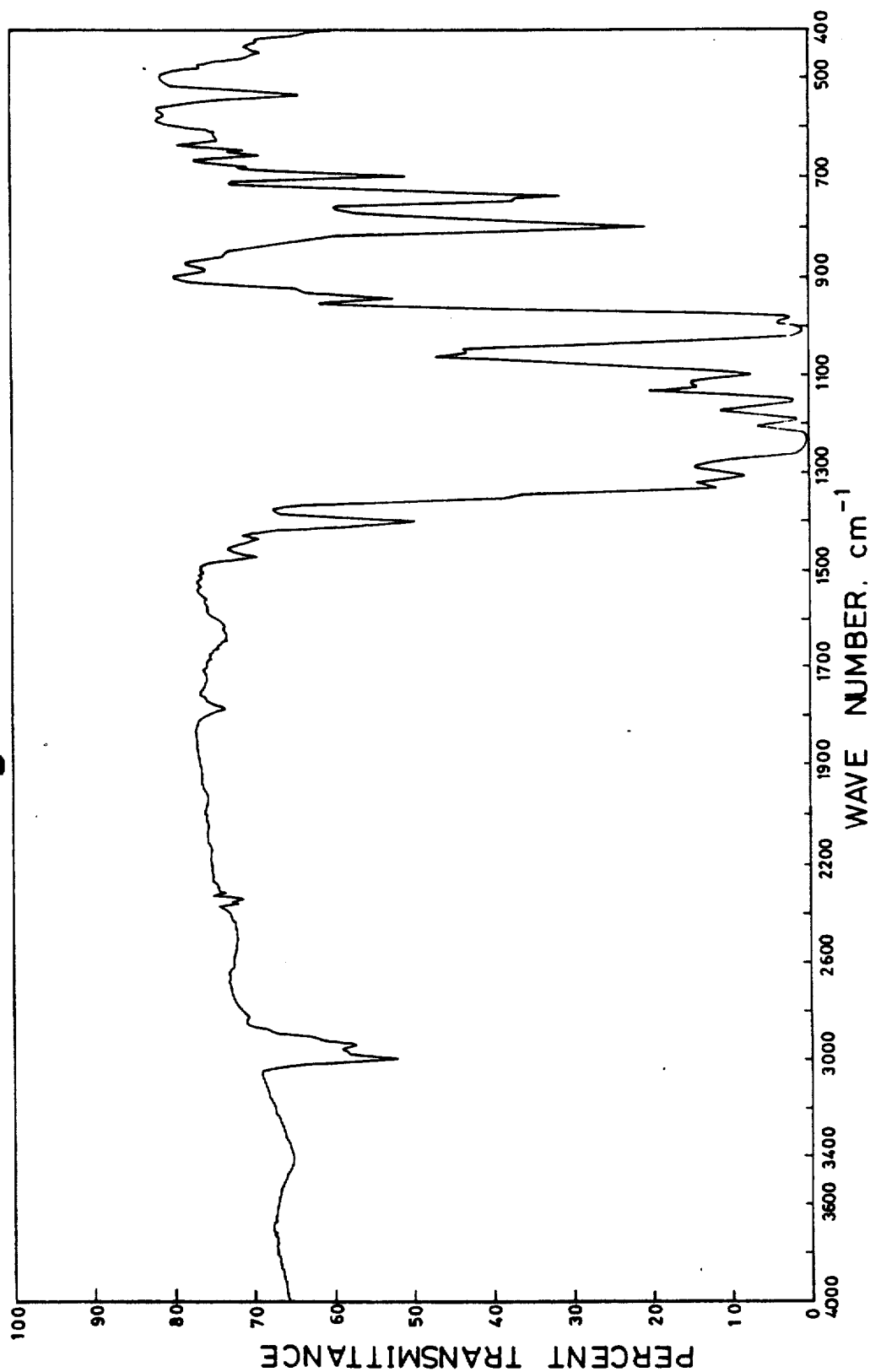
FIGS. 1 to 5 show IR spectra of the fluorine-containing organosilicon compound of this invention, obtained in Examples.

In Formula (I), Which represents the compound of this invention, the monovalent hydrocarbon group represented by $R^1$ includes, for example, a $C_1$ to $C_{10}$ alkyl group such as methyl, ethyl or propyl; a $C_6$ to $C_8$ aryl group such as a phenyl group, a tolyl group or a xylyl group: $C_7$ to $C_9$ aralkyl group such as a benzyl group; and an alpha-methylstyryl group. Preferable for the preparation of a fluorosiloxane polymer herein described below are a $C_1$ to $C_3$ alkyl group and a phenyl group, form the viewpoint of the resulting thermal resistance, chemical resistance, weathering resistance and so forth.

The fluorine-containing organosilicon compound of this invention can be synthesized in a high yield by, for example, subjecting a dichlorosilane compound represented by Formula (II):

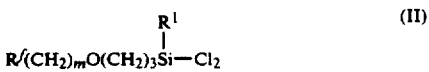

wherein $R^1$, $R^f$ and m are as defined above to hydrolysis and condensation under conditions described below.

More specifically, the compound of Formula (I) can be obtained in a high yield by carrying out the hydrolysis and condensation by use of a large excess of water in an amount of preferably from about 2 to 50 times (more preferably from about 5 to 20 times) on molar basis the amount of the dichlorosilane compound represented by Formula (II), and in the presence of an ether non-protonic organic polar solvent (as exemplified by diethyl ether, diisopropyl ether, diglyme, triglyme, tetragylme, tetrahydrofuran, and 1,4-dioxane) in an amount of preferably from about 1 to 10 times (more preferably from about 2 to 5 times) the compound in weight.

Also, the above hydrolysis and condensation may preferably be carried out under conditions in which the dichlorosilane compound of Formula (II) has been highly diluted to about 1 to 20 times in weight, and still more preferably from about 5 to 10 times in weight. For this purpose, it is desired to carry out the reaction under conditions in which the the dichlorosilane compound of Formula (II) has been diluted with a good solvent therefor as exemplified by fluorine solvents such as methaxylene hexafluoride, perfluorooctane, and 1,1,2-trichloro-1,2,2-trifluoroethane. There may be specifically included a method in which, for example, a fluorine solvent solution containing the above dichlorosilane compound of Formula (II) is slowly dropwise added to a system containing necessary amounts of the water, the ether non-protonic organic polar solvent and the above fluorine solvent.

The hydrolysis and condensation of the dichlorosilane compound of Formula (II) may preferably be carried out at a reaction temperature of from about 0 to 50° C., and more preferably from 10 to 30° C.

The dichlorosilane compound of Formula (II) can be prepared by, for example, the method as described in Japanese Unexamined Patent publication (KOKAI) No. 88359/1987.

The fluorine-containing organosilicon compound of this invention, represented by Formula (I) and having a cyclic siloxane structure is useful as a starting material for silicone fluids or elastomers. For example, in the same manner as hitherto known as conditions for ring opening polymerization of hexamethyltrisiloxane and octatmethyltetrasiloxane, a linear fluolosiloxane polymer is formed by carrying out open ring polymerization in the presence of an alkali catalyst such as KOH, CsOH or (n-Butyl)$_4$POH, or an acid catalyst such as H$_2$SO$_4$ or CF$_3$SO$_3$H. This linear fluorosiloxane polymer is useful as a starting material for various fluorosilicone fluids or elastomers.

In particular, the organosilicon compound of this invention, in which all the silicon atoms in the molecule have the side chain that contains many fluorine atoms, makes it possible to more enhance the thermal resistance, chemical resistance and weathering resistance of the resulting fluorosiloxane polymer, and, because of a small surface energy of the polymer, can further make higher also the level of the water repellency, oil repellency and release properties than those conventionally available. Also, because of a low refractive index, the compound promises to be used as materials for clad of optical fibers.

EXAMPLES

This invention will be described below in greater detail by way of Examples, but this invention is by no means limited to these.

Example 1

Into a four-necked flask equipped with a thermometer and a cooling tube and having an internal volume of 10 liter, 3,300 g of methaxylene hexafluoride, 370 g of water and 1,700 g of diethyl ether were put, which were mixed and stirred at 25° C. To the resulting mixed solution, a solution obtained by dissolving 862 g of a dichlorosilane compound represented by Formula (III):

(III)

in 1,000 g of methaxylene hexafluoride was slowly dropwise added through a dropping funnel at a dropping rate of about 1.4 g/min in terms of the weight of the dichlorosilane compound, to carry out hydrolysis and condensation. While the solution was dropwise added, the temperature of the reaction solution raised up to 30° C. at maximum because of reaction heats. After the solution had been dropwise added, the reaction mixture was stirred for 2 hours, to which 344 g of triethylamine was slowly added through a dropping funnel to neutralize the reaction mixture. The resulting reaction product was washed with water to remove a by-product triethylamine hydrochloride, followed by separation of the organic layer and distillation of the separated organic layer under reduced pressure to obtain 553 g of Compound (IV) as a fraction of 159–161° C./1 Torr and 139 g of Compound (V) as a fraction of 205–208° C./1 Torr. Next, these Compounds (IV) and (V) were subjected to elementary analysis and also measurement of IR spectra, GC-MS spectra and $^1$H-NMR spectra to obtain the following analytical results, from which the resulting Compounds (IV) and (V) were confirmed to be the fluorine-containing organosilicon compounds represented by the following formulas, respectively.

Compound (IV):

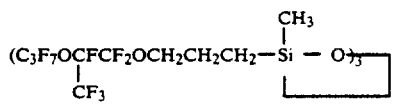

Elementary analysis:

|  |  | C | H | Si | F | O |
|---|---|---|---|---|---|---|
| Calculated* | (%) | 26.56 | 2.01 | 6.21 | 54.61 | 10.61 |
| Found | (%) | 26.58 | 2.00 | 6.22 | 54.61 | 10.59 |

*as C$_{30}$H$_{27}$Si$_3$F$_{39}$O$_9$

IR spectrum: As shown in FIG. 1.
Characteristic absorption (cm$^{-1}$):
1,020 (Si-O), 1,000–1,400 (C-F)
GC-MS spectrum: (M/e)
Molecular weight: 1,357 (M+) $^1$H-NMR spectrum: δ (ppm) (Internal standard: CHCl$_3$)
  0.35–0.80 (m, 6H, Si—CH$_2$—C)
  1.58–1.99 (m, 6H, C—CH$_2$—C)
  3.81–4.11 (t, 6H, C—CH$_2$—O)
Yield: 72.0%

Compound (V):

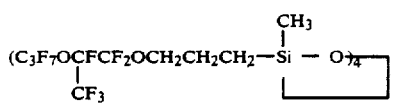

Elementary analysis:

|  |  | C | H | Si | F | O |
|---|---|---|---|---|---|---|
| Calculated* | (%) | 26.56 | 2.01 | 6.21 | 54.61 | 10.61 |
| Found | (%) | 26.57 | 2.02 | 6.20 | 54.60 | 10.61 |

*as C$_{40}$OH$_{36}$Si$_4$F$_{52}$O$_{12}$

Figure 2:
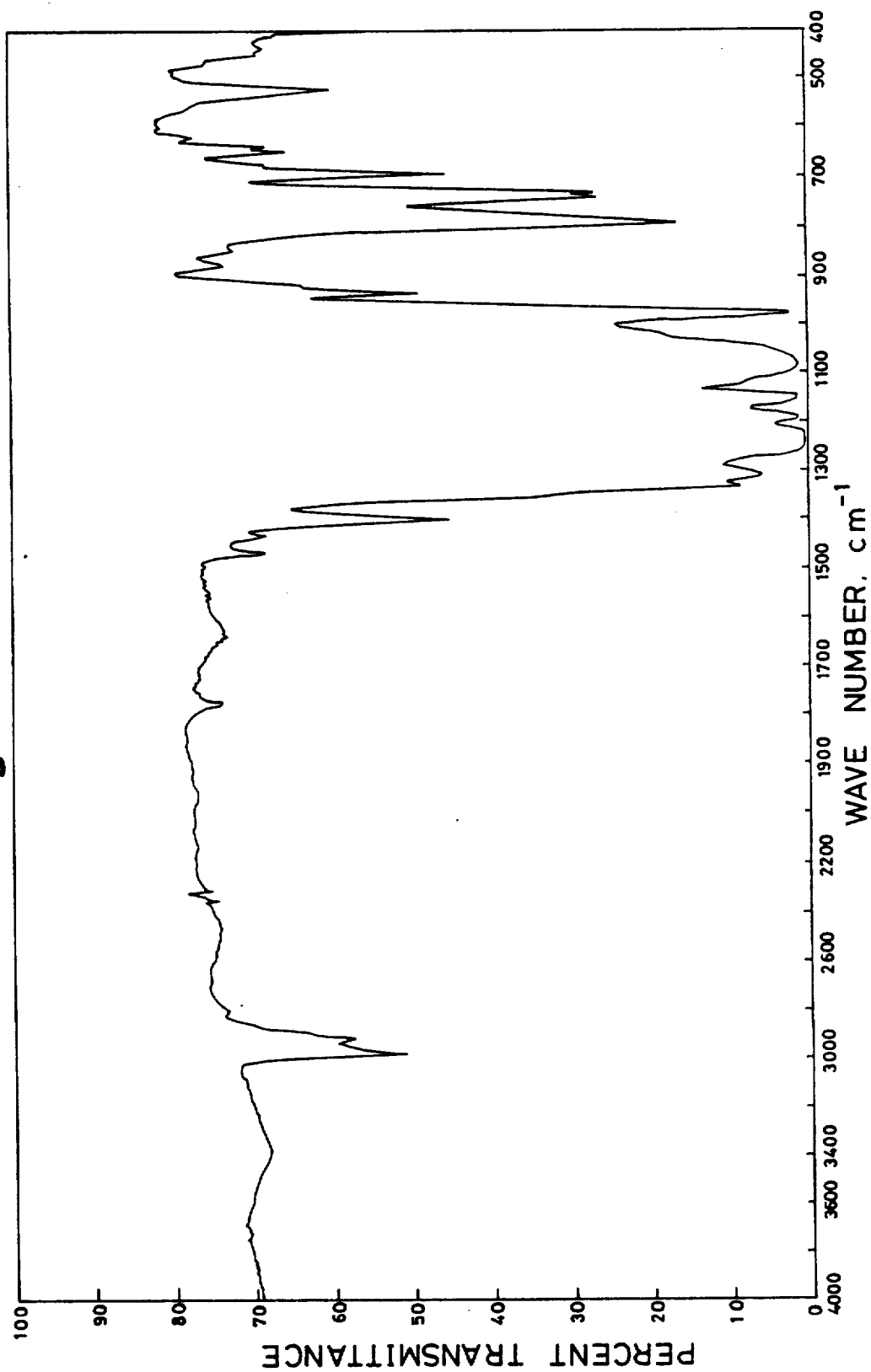

IR spectrum: As shown in FIG. 2.
Characteristic absorption (cm$^{-1}$):
1,080–1,090 (Si-O), 1,000–1,400 (C-F)
GC-MS spectrum: (M/e)
Molecular weight: 1,809 (M+) $^1$H-NMR spectrum: δ (ppm) (Internal standard: CHCl$_3$)
  0.36–0.81 (m, 8H, Si—CH$_2$—C)
  1.57–1.97 (m, 8H, C—CH$_2$—C)
  3.81–4.10 (t, 8H, C—CH$_2$—O)
Yield: 18.1%

Example 2

Into a four necked flask equipped with a thermometer and a cooling tube and having an internal volume of 10 liter, 4,800 g of methaxylene hexafluoride, 525 g of water and 2,440 g of diethyl ether were put, which were mixed and stirred at 25° C. To the resulting mixed solution, a solution obtained by dissolving 1,140 g of a dichlorosilane compound represented by Formula (VI):

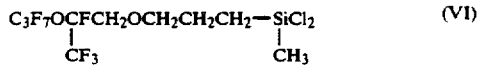
(VI)

in 800 g of methaxylene hexafluoride was slowly dropwise added through a dropping funnel at a dropping rate of about 2.8 g/min in terms of the weight of the dichlorosilane compound, to carry out hydrolysis and condensation. After the solution had been dropwise added, the reaction mixture was stirred for 2 hours, to which 490 g of triethylamine was added through a dropping funnel to neutralize the reaction mixture. The resulting reaction product was washed with water to remove a by-product triethylamine hydrochloride, followed by separation and then distillation of the organic layer under reduced pressure to obtain 666 g of Compound (VII) as a fraction of 169–171° C./1 Torr and 278 g of Compound (VIII) as a fraction of 208–212° C./1 Torr. Next, these Compounds (VII) and (VIII) were subjected to elementary analysis and also measurement of IR spectra, GC-MS spectra and $^1$H-NMR spectra to obtain the following analytical results, from which the resulting Compounds (VII) and (VIII) were confirmed to be the fluorine-containing organosilicon compounds represented by the following formulas, respectively.

Compound (VII):

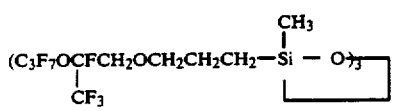

Elementary analysis:

|  |  | C | H | Si | F | O |
|---|---|---|---|---|---|---|
| Calculated* | (%) | 28.85 | 2.66 | 6.75 | 50.20 | 11.54 |
| Found | (%) | 28.87 | 2.65 | 6.74 | 50.19 | 11.55 |

*as $C_{30}H_{33}Si_3F_{33}O_9$

Figure 3:
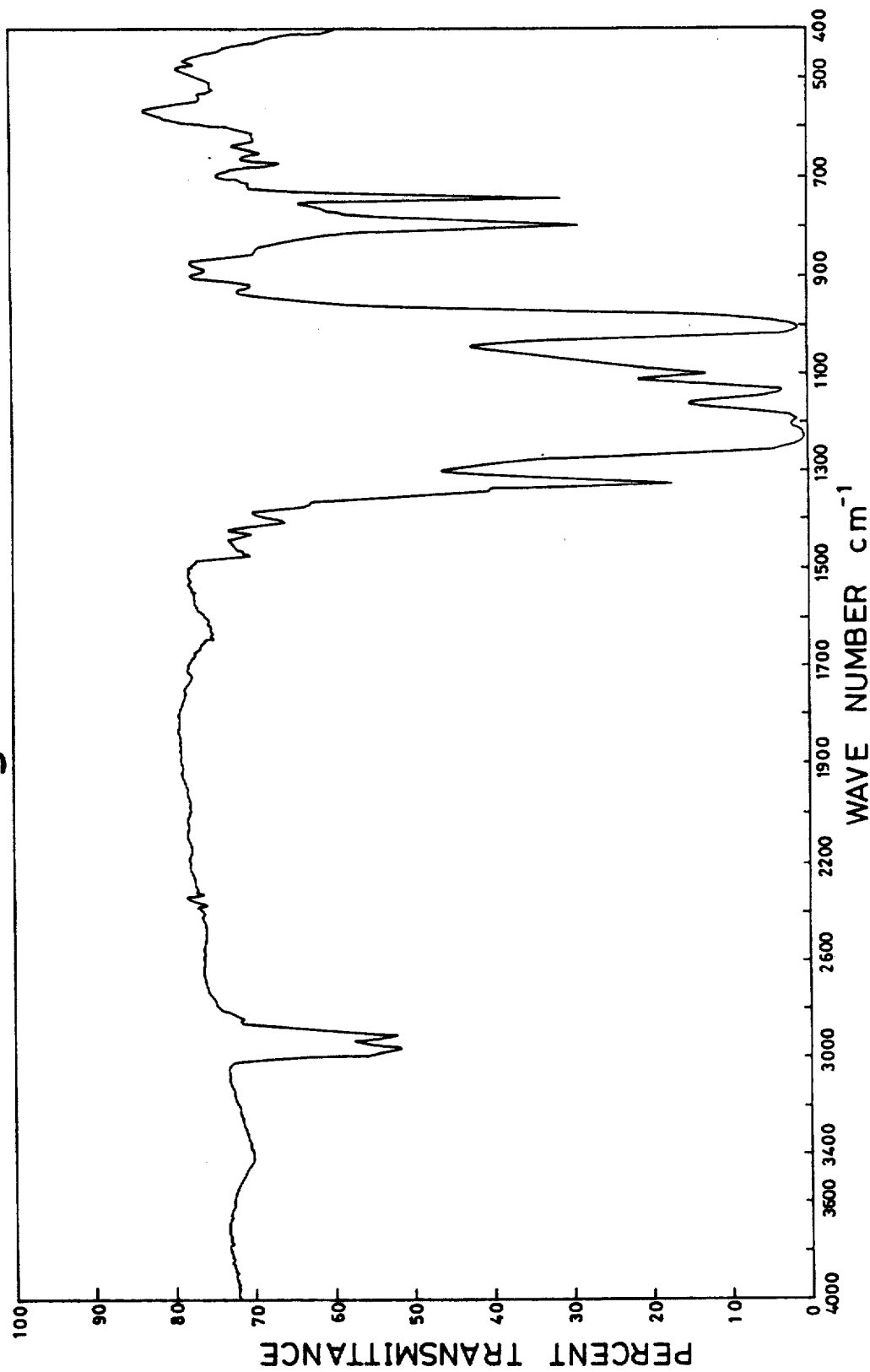

IR spectrum: As shown in FIG. 3.
Characteristic absorption (cm$^{-1}$):
1,020 (Si-O), 1,000–1,400 (C-F)
GC MS spectrum: (M/e)
Molecular weight: 1,249 (M+) $^1$H-NMR spectrum: δ (ppm) (Internal standard: CHCl$_3$)
0.40–0.73 (m, 6H, Si—CH$_2$—C)
1.37–1.93 (m, 6H, C—CH$_2$—C)
3.37–3.67 (t, 6H, C—CH$_2$—O)
3.77–4.10 (d, 6H, C—CH$_2$—CF)
Yield: 66.2%

Compound (VIII):

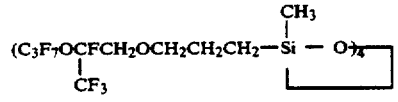

Elementary analysis:

|  |  | C | H | Si | F | O |
|---|---|---|---|---|---|---|
| Calculated* | (%) | 28.85 | 2.66 | 6.75 | 50.20 | 11.54 |
| Found | (%) | 28.85 | 2.67 | 6.74 | 50.21 | 11.53 |

*as $C_{40}H_{44}Si_4F_{44}O_{12}$

Figure 4:
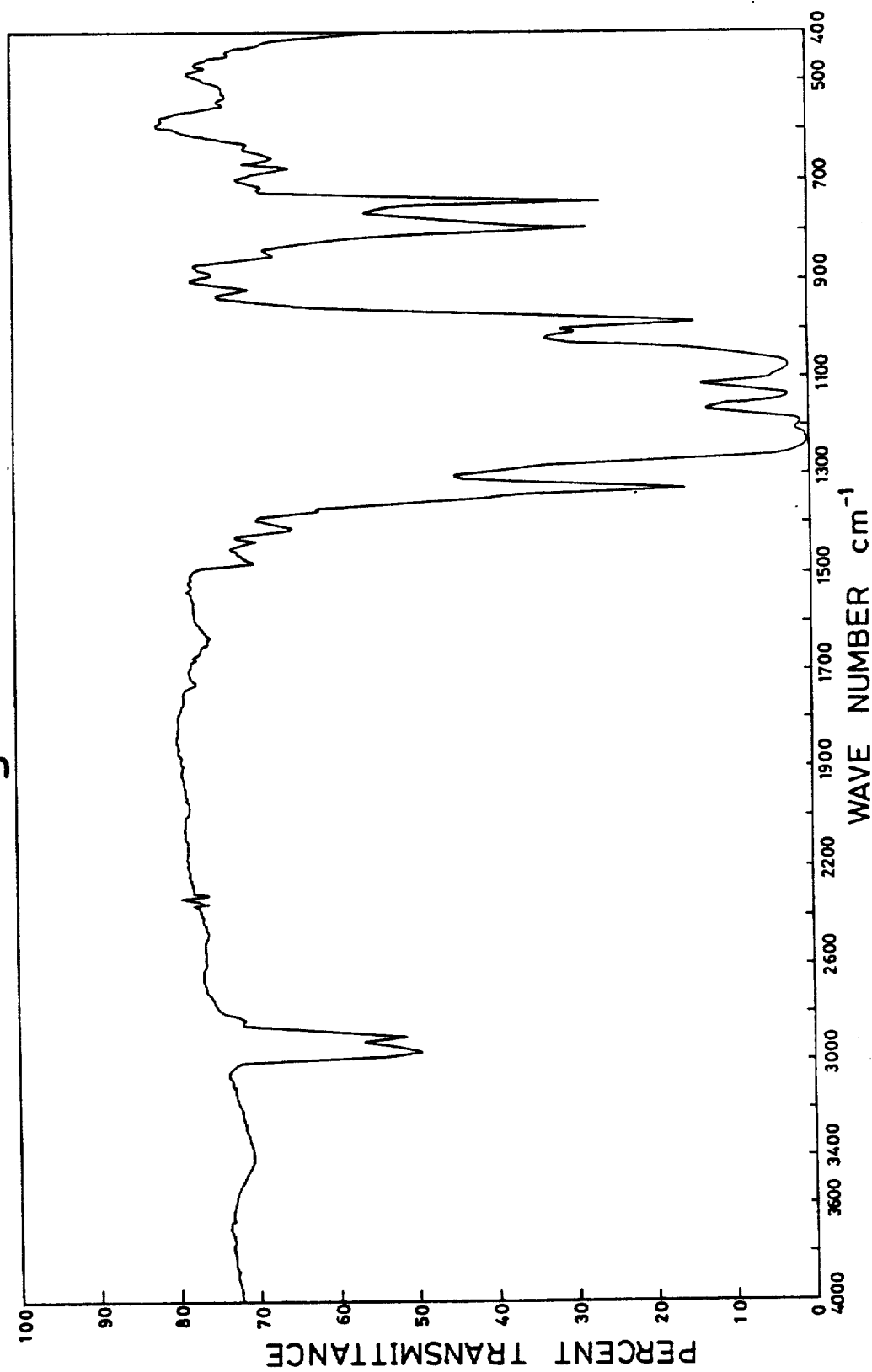

IR spectrum: As shown in FIG. 4.
Absorption characteristics (cm$^{-1}$):
1,080 (Si-O), 1,000–1,400 (C-F)
C-MS spectrum: (M/e)
Molecular weight: 1,665 (M+) $^1$H-NMR spectrum: δ (ppm) (Internal standard: CHCl$_3$)
0.40–0.74 (m, 8H, Si—CH$_2$—C)
1.36–1.92 (m, 8H, C—CH$_2$—C)
3.37–3.68 (t, 8H, C—CH$_2$—O)
3.78–4.11 (d, 8H, C—CH$_2$—CF)
Yield: 27.6%

Example 3

Example 1 was repeated but except that 320 g of a dichlorosilane compound represented by Formula (IX):

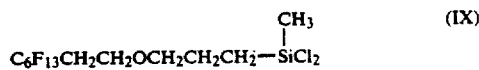

was used in place of the dichlorosilane compound represented by Formula (III), to obtain 195 g of Compound (X) as a fraction of 223–225° C./1×10$^{-5}$ Torr. Next, this Compound (X) was subjected to elementary analysis and also measurement of IR spectrum, GC-MS spectrum and $^1$H-NMR spectrum to obtain the following analytical results, from which the resulting Compound (X) was confirmed to be the fluorine-containing organosilicon compound represented by the following formula.

Compound (X):

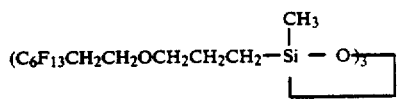

Elementary analysis:

|  |  | C | H | Si | F | O |
|---|---|---|---|---|---|---|
| Calculated* | (%) | 31.04 | 2.82 | 6.05 | 53.19 | 6.90 |
| Found | (%) | 31.02 | 2.83 | 6.06 | 53.20 | 6.89 |

*as $C_{36}H_{39}Si_3F_{39}O_6$

Figure 5:
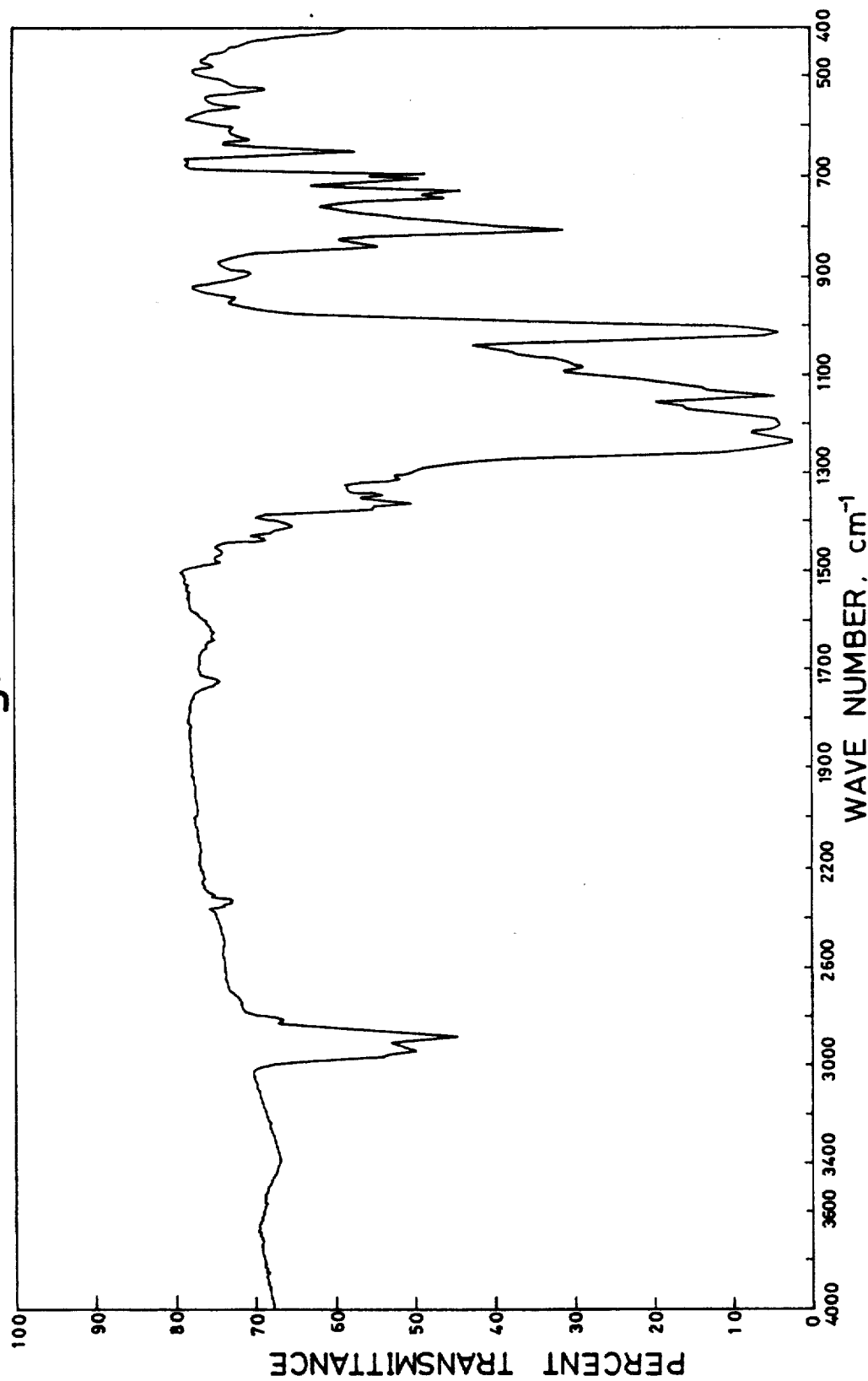

IR spectrum: As shown in FIG. 5.
Characteristic absorption (cm$^{-1}$):
1,010 (Si—O), 1,000–1,400 (C—F)
GC-MS spectrum: (M/e)
Molecular weight: 1,393 (M+)
$^1$H-NMR spectrum: δ (ppm) (Internal standard: CHCl$_3$)
0.37–0.75 (m, 6H, Si—CH$_2$—C)
1.33–1.85 (m, 6H, C—CH$_2$—C)
2.08–2.83 (m, 6H, C—CH$_2$—CF)
3.22–3.82 (m, 12H, C—CH$_2$—O)
Yield: 67.9%

We claim:
1. A fluorine-containing organosilicon compound having the formula (I):

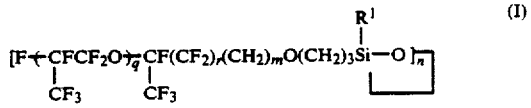

wherein R' represents a monovalent hydrocarbon group having 1 to 10 carbon atoms, m is an integer of 0 to 2, n is an integer of 3 or 4, q is an integer of 1 or 2, and r is an integer of 0 or 1.

2. The compound according to claim 1, wherein R$^1$ in formula (I) represents a C$_1$ to C$_{10}$ alkyl group, a C$_6$ to C$_8$ aryl group, a C$_7$ to C$_9$ aralkyl group or an alpha-methylstyryl group.

3. The compound according to claim 1, wherein R$^1$ in formula (I) represents a methyl group or a phenyl group.

4. The compound according to claim 1, wherein R' represents a C$_1$–C$_3$ alkyl group.